United States Patent [19]

Buzas

[11] 4,353,911
[45] Oct. 12, 1982

[54] INDOLO(2,3-A)QUINOLIZIDINES, USEFUL IN INCREASING FEMORAL AND VERTEBRAL BLOOD FLOW

[76] Inventor: Andre Buzas, 25, Route de Versailles, 91570 Bievres, France

[21] Appl. No.: 129,974

[22] PCT Filed: Nov. 24, 1978

[86] PCT No.: PCT/FR78/00043

§ 371 Date: Jul. 25, 1979

§ 102(e) Date: Jul. 20, 1979

[87] PCT Pub. No.: WO79/00319

PCT Pub. Date: Jun. 14, 1979

[51] Int. Cl.$^3$ .................. A61K 31/475; C07D 401/02
[52] U.S. Cl. .................................... 424/258; 546/70; 546/71
[58] Field of Search ................ 546/70, 71; 424/258, 424/2, 8

[56] References Cited

U.S. PATENT DOCUMENTS

| | | | |
|---|---|---|---|
| 3,830,823 | 8/1974 | Castaigne | 546/70 |
| 3,962,258 | 6/1976 | Archibald et al. | 546/70 |
| 4,044,012 | 8/1977 | Szantay et al. | 546/70 |
| 4,052,404 | 10/1977 | Szantay et al. | 546/70 |
| 4,057,551 | 11/1977 | Szantay et al. | 546/70 |
| 4,173,642 | 11/1979 | Szantay et al. | 546/70 |

FOREIGN PATENT DOCUMENTS 2317304  3/1977  France .................... 546/70

Primary Examiner—David B. Springer
Attorney, Agent, or Firm—Eyre, Mann, Lucas & Just

[57] ABSTRACT

The invention is a method of increasing femoral blood flow and vertebral blood flow a compound of the formula:

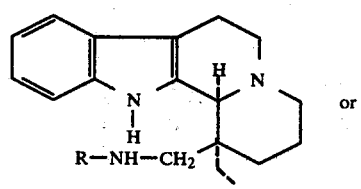

or

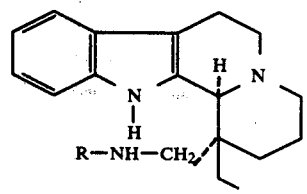

wherein R is alkoxy carbonyl the alkoxy having up to 5 carbon atoms, trimethoxy substituted phenyl carbonyl or a therapeutically acceptable acid addition salt of one of the foregoing.

2 Claims, No Drawings

INDOLO(2,3-A)QUINOLIZIDINES, USEFUL IN INCREASING FEMORAL AND VERTEBRAL BLOOD FLOW

The invention relates to indolo(2,3-a)quinolizidines, to methods for their preparation and to therapeutic compositions containing them.

The new indolo(2,3-a)quinolizidines according to the invention have the general formulae (I) and (II)

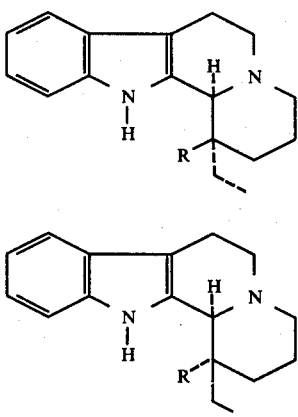

wherein R stands for $-COOC_2H_5-$, $COOH-$, $CN$, a primary or secondary methylenamino group, a methylenamido group, or wherein R, together with the ring nitrogen of the indole ring, represents one of the groups $N-CO-NH-CH_2$ or $N-CO-$; the latter derivatives are D-homo-azaeburnamonines or D-eburnamonines.

The invention also relates to acid addition salts of the above compounds, when applicable.

R may be, for example, a methylenaminocarbalkoxy group, a methylenaminoaryloxycarbonyl group, a methylenaminoalkanoyl group, a methylenaminoalkyl group or a substituted methylenureido group.

Preferred identities of R according to this invention are COOH, $NH_2$, methylenaminocarbethoxy, methylenamino-(3,4,5-trimethoxy)benzoyl, methylenaminophenoxycarbonyl, methylenureidodiethylaminoethyl, methylenaminopentanoyl, methylenaminopentyl and amidopiperonyl.

The compounds according to this invention are especially interesting for their activity in the field of blood circulation in the brain. The invention accordingly provides therapeutic compositions comprising one or more such compounds in admixture with a therapeutically acceptable diluent or carrier.

The above compounds may be prepared according to the invention by condensing 3-(2'-aminoethyl)indole with 1-chloro-4-(A)-4-chlorocarbonyl-hexane, wherein A stands for $-COOC_2H_5$ or $-CN$, to form the corresponding amide; subjecting the amide to strongly basic conditions to eliminate HCl and effect ring formation at the nitrogen atom on the 3-substituent of the indole; effecting quinolizidine ring formation of the product by treating it with a dehydrating agent followed by a perchlorate salt; hydrogenating the resulting quinolizidinium perchlorate to produce the corresponding indolo(2,3-a)quinolizidine isomer mixture and separating the isomers; the corresponding reaction schemes are represented hereafter under the heading "Initial Common Routes" and lead only to the compounds wherein R is $-COOC_2H_5$ or $-CN$ (2 isomeric forms in each case, i.e., 4 compounds).

All the other derivatives are obtained from these compounds
either directly, e.g. the acids, from the esters, by saponification (see the schemes "Specific Reactions" $A=-COOC_2H_5$), or the methylenamino derivative from the nitriles, by reduction with lithium aluminium hydride (see same schemes when $A=-CN$),
or from the acids or methylamino derivatives, by well known reactions.

In the following schemes:

I is a reference to cis-isomers

II is a reference to trans-isomers

1(a) to 1(i) are references to the various steps of example 1 wherein the starting material is the 4-ethoxycarbonyl derivative and the final products are acids or derivatives thereof and 2(a) to 2(g) are references to the various steps of example 2 wherein the starting material is the 4-cyano derivative and the final products are methylamino derivatives thereof.

Initial Common reactions

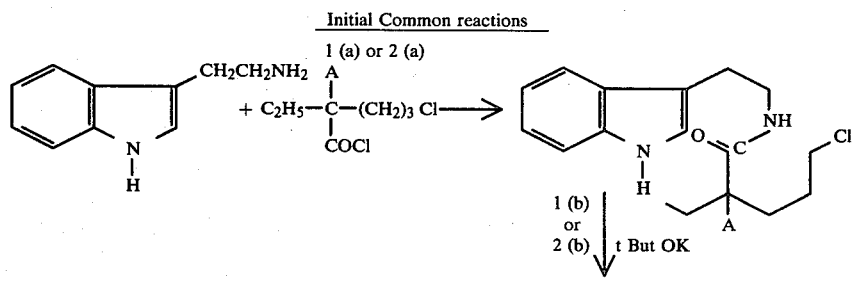

-continued
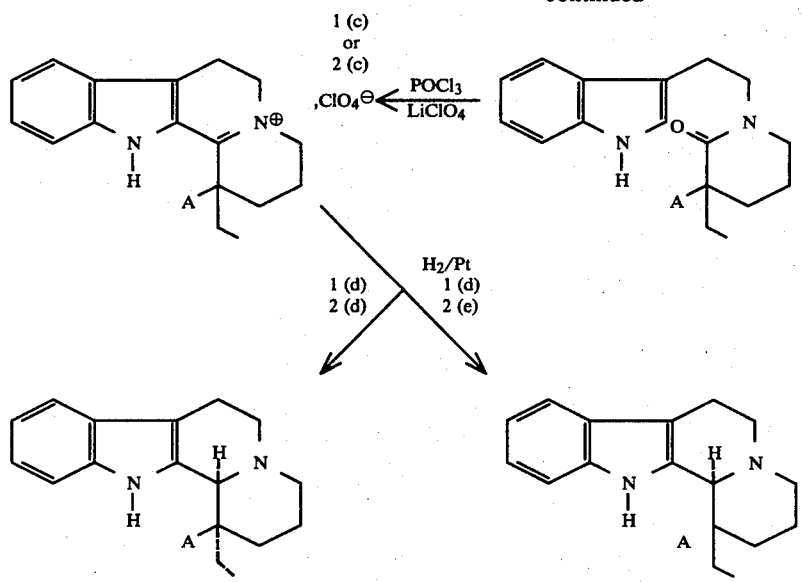
Specific reactions
A = —COOC₂H₅
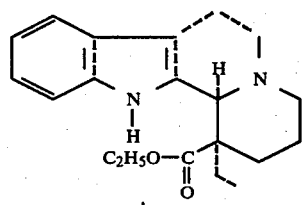
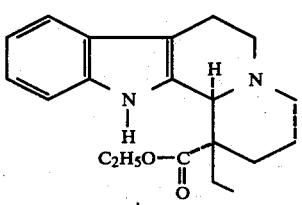
1 (h) ↓ KOH          1 (e) ↓ KOH
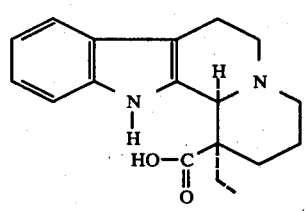
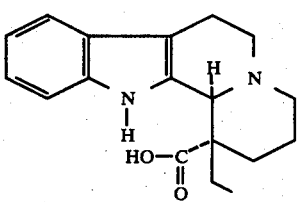
(I)                    (II)
A = —CN
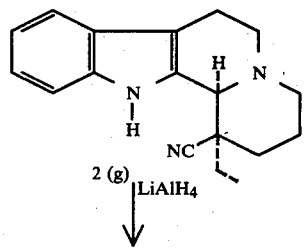
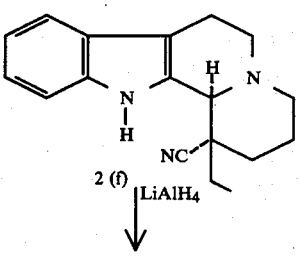
2 (g) ↓ LiAlH₄        2 (f) ↓ LiAlH₄
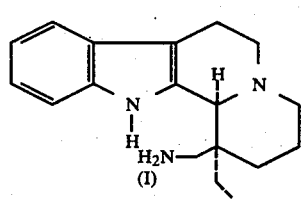
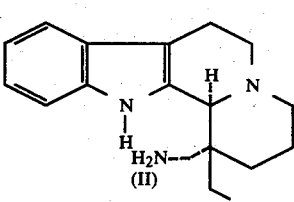
(I)                    (II)
The invention is illustrated by the following Examples.

(a) Preparation of 3-[2'-(2''-ethoxycarbonyl-2''-ethyl-5''-chloro-valeroylamino)-ethyl]-indole To a suspension of 2.5 g (0.0184 mole) of 3-(2'-aminoethyl)indole (tryptamine) in 50 ml dry chloroform containing 2 g (0.02 mole) of triethylamine cooled in an ice bath there were added drop by drop 4.7 g (0.0184 mole) of 2-ethyl-2-ethoxycarbonyl-5-chloro-valeroyl chloride. After stirring for 2 hours at room temperature, the solution was washed with dilute aqueous hydrochloric acid. After drying the organic phase and evaporating it under reduced pressure there was obtained 6.6 g of the above product which, recrystallized from a mixture of petroleum ether/isopropyl ether, melted at 76° C. and had a yield of 95%. The results of analysis were as follows:

IR (KBr) 3350 and 3300 cm$^{-1}$, NH; 1735 cm$^{-1}$, CO ester; 1640 cm$^{-1}$, CO amide. Calculated for $C_{20}H_{27}N_2O_3Cl$: C=63.40%; H=7.18%; N=7.40% Found: C=63.39%; H=7.05%; N=7.51%.

(b) Preparation of 1-[(2'-indol-3''-ylethyl)-3-ethyl-3-ethoxycarbonyl]-2-piperidone To a suspension of 34.4 g (0.0908 mole) of the above compound in 150 ml of a 1:1 mixture of dry benzene and hexamethylphosphoric/triamide cooled in an ice bath there was added, in small quantities and in a nitrogen atmosphere, 10.6 g (0.0946 mole) of potassium t-butoxide. After stirring for 8 hours at room temperature, the solution was poured into a cold dilute solution of hydrochloric acid. The aqueous phase, after decantation, was extracted two times with benzene. The resulting organic phase was washed twice with water and dried. After evaporating under reduced pressure there was obtained 30 g of the desired product which, recrystallized from isopropyl ether, melted at 84° F. and had a yield of 96%. The results of analysis were as follows:

IR (KBr) 3250 cm$^{-1}$, NH indole; 1730 cm$^{-1}$, CO ester; 1620 cm$^{-1}$, CO amide; Calculated for $C_{20}H_{26}N_2O_3$: C=70.15%; H=7.65%; N=8.13% Found: C=69.97%; H=7.65%; N=8.20%.

(c) Preparation of 1-ethyl-1-ethoxycarbonyl-5,12b-didehydro-indolo(2,3-a)quinolizidinium perchlorate Into a solution of 30 g (0.0876 mole) of the above compound in 480 ml of dry toluene there were poured 240 ml of distilled phosphoryl chloride. This solution was heated under reflux for 9 hours with a moisture guard. Excess phosphoryl chloride and toluene were then removed under reduced pressure. The residue was taken up in methylene dichloride and the solution was washed with water, dried over sodium sulphate and evaporated under reduced pressure. A part of the solution was agitated with a 1 M aqueous solution of lithium perchlorate. After decanting the aqueous phase, washing the organic phase with water, drying over sodium sulphate and evaporating the solvent under reduced pressure there was obtained a yellow powder which was recrystallized from ethanol. The resulting product melted at 191° F. The results of analysis were as follows:

IR (KBr) 3340 cm$^{-1}$, NH; 1740 cm$^{-1}$, CO ester; 1625 cm$^{-1}$, C=N<$\oplus$.

(d) Preparation of 1-ethyl-1-ethoxycarbonyl-indolo(2,3-a)quinolizidine (12b-H; 1-$C_2H_5$ trans and cis-isomers)

A solution of 6.25 g (0.0147 mole) of the above perchlorate salt in 80 ml of ethanol was hydrogenated for 12 hours in the presence of 0.3 g of platinum oxide. After filtration, the ethanol was evaporated under reduced pressure and the residue taken up in methylene chloride and stirred with 5% sodium hydroxide. The organic phase was decanted and washed with distilled water.

On chromatography of a solution of the product with methylene chloride over 100 grams of silica, and elution with the same solvent, there was separated 1.12 g of a first fraction (yield 25%) which was the 12b-H; 1-$C_2H_5$ trans-isomer of the product and melted at 112° C. (recrystallized from petroleum ether/isopropyl ether). The results of analysis were as follows:

IR (KBr) 3410 cm$^{-1}$, NH; 2270, 2805, 2825 cm$^{-1}$, Bohlmann bands; 1710 cm$^{-1}$ CO ester.

NMR (CDCl$_3$ 90 MHz):
among other signals: 8.5δ OH (s) (N$\underline{H}$ indole), 4.35δ 2H (q) (O—C$\underline{H_2}$—CH$_3$), 3.85δ 1H (s) ($\underline{H}$ on C$_{9a}$), 1.35δ 3H (t) (C$\underline{H_3}$—CH$_2$—O—), 0.75δ 3H (t) (C$\underline{H_3}$—CH$_2$); Calculated for $C_{20}H_{26}N_2O_2$: C=73.59%; H=8.03%; N=8.58% Found: C=73.47%; H=8.12%; N=8.33%.

The later fractions of chromatography gave 1.8 g of an oil which was the 12b-H; 1-$C_2H_5$ cis-isomer of the desired product.

The results of analysis were as follows:
IR (KBr) 3420 cm$^{-1}$, NH; 3750, 3800 cm$^{-1}$, Bohlmann bands; 1705 cm$^{-1}$, CO ester.

NMR (CCl$_4$ 90 MHz)
among other signals: 7.78δ 1H (s) (N$\underline{H}$ indole), 4.15δ 2H (q) (—OC$\underline{H_2}$—CH$_3$), 3.93δ 1H (s) ($\underline{H}$ on C$_{9a}$), 1.09δ 3H (t) (C$\underline{H_3}$—CH$_2$—O), 0.9δ 3H (t) (C$\underline{H_3}$—CH$_2$—).

The hydrochlorides, recrystallized from isopropanol, melted above 260° C.
Calculated for $C_{20}H_{26}N_2O_2 \cdot HCl \cdot 1.5\ H_2C$: C=61.57%; H=7.75%; N=7.18% Found: C=61.51%; H=7.33%; N=7.35%.

(e) Preparation of 1-ethyl-1-carboxy-indolo(2,3-a)quinolizidine (12b-H; 1C$_2$H$_5$ trans-isomer) hydrochloride

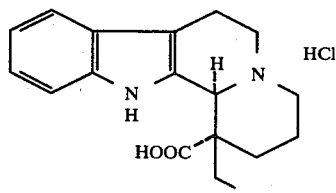

To a solution of 8.8 g of the ester obtained in step (d) above in 100 ml of ethanol are added 8.8 g of KOH and the mixture is refluxed for 12 hours. The solvent is eliminated under reduced pressure and the residue taken up in ice water, acidified with concentrated hydrochloric acid until an acid pH is reached; the hydrochloride precipitates, is separated, washed and dried. Yield 9.5 g (100%) of the product crystallized with 1 mole of H$_2$O. M.P.: >260° C.

Analysis   Formula $C_{18}H_{22}N_2O_2$, HCl, H$_2$O   M.W.: 353.

-continued

|  | C | H | N |
|---|---|---|---|
| Calculated | 61.20% | 7.08% | 7.93% |
| Found: | 61.01% | 6.75% | 7.72%. |
| IR (KBr) | 3340 cm$^{-1}$ | NH | |
| | 1705 cm$^{-1}$ | (—C—OH) ‖ O | |

(f) Preparation of 1-ethyl-1-piperonylpiperazidocarbonyl-indolo(2,3-a)quinolizidine (12b-H; 1-C$_2$H$_5$ trans-isomer) dihydrochloride

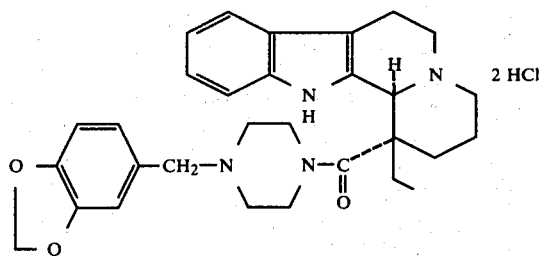

6 g of the hydrochloride of step (e) above are suspended in 50 ml of benzene and there are added, while cooling, 40 ml of oxalyl chloride. After stirring for 24 hours at 40° C., the excess oxalyl chloride is eliminated by distillation under reduced pressure and the residue is taken up four times in dry benzene. The dry residue is then suspended in 50 ml of methylene chloride and cooled at 0° C. A solution of 3.6 g of piperonylpiperazine and 3.4 g of triethylamine in 20 ml of methylene chloride are added and the mixture is stirred for 6 hours at room temperature. After filtration of the insoluble matter and elimination of the methylene chloride, the residue is treated on a colloidal silica column (eluent CH$_2$Cl$_2$). 4.9 g (yield: 60%) of an oily product are obtained.

IR (film) 3360 cm$^{-1}$ (NH); 1640 cm$^{-1}$ (CO).

NMR (COCl$_3$, internal standard TMS) δ in 10$^{-6}$: 9.2 1s (1H) NH indole, 5.9 1s (2H) O—CH$_2$—O, 4.05 1s (1H) H(C$_{12b}$), 0.3 1t (3H) CH$_3$—CH$_2$.

The dihydrochloride is obtained by treatment with aqueous alcoholic HCl; crystallization with 3H$_2$O. Melting point 242° C.

| Analysis C$_{30}$H$_{36}$N$_4$O$_3$, 2HCl, 3H$_2$O M.W.: 627.6 | | | |
|---|---|---|---|
| | C | H | N |
| Calculated | 57.40 | 7.01 | 8.92 |
| Found: | 57.82 | 6.55 | 8.64 |

(g) Preparation of 1-ethyl-1[4-(trimethoxybenzamido)piperazinocarbonyl-]indolo(2,3-a)quinolizidine-(12b-H; 1-C$_2$H$_5$ trans-isomer) hydrochloride

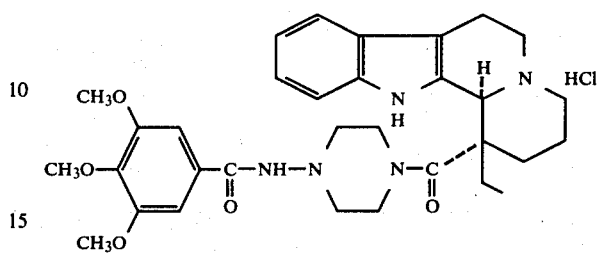

5 g of hydrochloride of step (e) above are treated with oxalyl chloride as described in step (f) above. 5.3 g of dry residue are obtained, to which are added 50 ml of methylene chloride and the mixture is cooled at 0° C. A solution of 3 g of triethylamine and 3 g of 4-(trimethoxybenzoylamino)-1-piperazine in 20 ml of methylene chloride. The mixture is stirred for 24 hours at room temperature, then washed with a 10% aqueous sodium hydroxide solution, then with water, dried and the excess solvent is eliminated. 7.2 g of an oily product are obtained.

IR (film) 3380 cm$^{-1}$ and 3240 cm$^{-1}$ (NH), 1650 cm$^{-1}$ and 1620 cm$^{-1}$ (CO).

The hydrochloride is obtained by treatment with aqueous alcoholic HCl.
M.P.: 225° C.

| Analysis C$_{32}$H$_{41}$N$_5$O$_5$, HCl M.W.: 611 | | | |
|---|---|---|---|
| | C | H | N |
| Calculated | 62.87 | 6.92 | 11.46 |
| Found | 62.24 | 6.95 | 11.18 |

(h) Preparation of 1-ethyl-1-carboxy-indolo(2,3-a)quinolizidine (12b-H; 1-C$_2$H$_5$ cis-isomer)

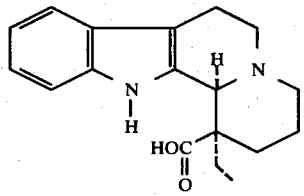

Into a solution of 6.8 g of 1-ethyl-1-ethoxycarbonyl-indolo(2,3-a)quinolizidine (12b-H; 1-C$_2$H$_5$ cis-isomer) obtained in the preceding example (d), in 100 ml of 95% ethanol, there are added 6.8 g of potassium hydroxide. The mixture is refluxed for 12 hours, the solvent evaporated under reduced pressure and the residue taken up in ice water and acidified with HCl to pH=4.5. The precipitated product is separated, washed and dried. 4.1 g of acid are thus obtained.

| Analysis C$_{18}$H$_{22}$N$_2$O$_2$ M = 298.37 | | | |
|---|---|---|---|
| | C | H | N |
| Calculated | 72.45 | 7.43 | 9.37 |

-continued

| Analysis C₁₈H₂₂N₂O₂ M = 298.37 | | | |
|---|---|---|---|
| | C | H | N |
| Found | 72.61 | 7.49 | 9.20 |

IR 1620 cm⁻¹ ν CO, OH associated.

(i) Preparation of (+)-D-noreburnamonine

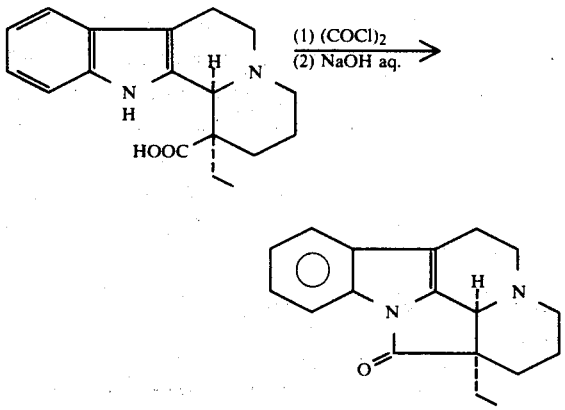

30 ml of oxalyl chloride are added, dropwise, to a suspension of 6 g (0.0179 mole) of 1-ethyl-1-carboxy-indolo(2,3-a)quinolizidine (12b-H; 1-C₂H₅ cis-isomer) of step (h) above, in 60 ml of dry benzene. The suspension is stirred for 2 hours at room temperature, then refluxed for 9 hours. The solvents are eliminated under reduced pressure and the residue is taken up in methylene chloride, and stirred in the presence of dilute sodium hydroxide. The organic solution, washed with water, dried on sodium sulphate and evaporated at reduced pressure, gives 4.25 g of the product sought.
Yield 83%.

After washing on an alumina column, 3.25 g of beige crystals are obtained. M.P.=136° C. (isopropyl ether).
IR (KBr): 2805, 2845, 1735, 1660 cm⁻¹, C₁₈H₂₀N₂O=280,96. Calculated %: C 77.11, H=7.19, N 9.99; Found: 77.54, 7.78, 10.09.
H₁RMN (COCl₃) internal standard. TMS δ$_{TMS}$=0 7.9-7.7 (m) aromatic; 7.5-7.05 (m) 3H aromatic; 4.3 (m) 1H; 1.1 (t) CH₃—CH₂.

Hydrochloride

The necessary amount of aqueous 7 N HCl is added to a solution of 3.25 g of base in 30 ml of absolute alcohol. The solvents are evaporated under reduced pressure, at 30° C. and the residue, taken up in acetone, gives 3.32 g of a white crystalline product. M.P.: 264° C.
IR (KBr): 3400, 2470, 2320, 1740, 1680 cm⁻¹
C¹³RMN (D₂O) standard: dioxane δppm 107.426 C≡O; −13.712 CH; −82.162 CH₃.

EXAMPLE 2

(a) Preparation of 3-[2'-(2''-cyano-2''-ethyl-5''-chloro-valeroylamino)ethyl]-indole In a 1 liter flask there were placed 31 g (0.194 mole) of tryptamine 500 ml of dichloromethane and 20 g (0.198 mole) of triethylamine. The mixture was cooled on ice to 0° C. and there were added 40 g (0.192 mole) of 2-cyano-2-ethyl-5-chloro-valeroyl chloride dissolved in 150 ml of methylene chloride. After 2 hours at room temperature the mixture was washed with water, then with 10% hydrochloric acid, and then with 10% sodium hydroxide. It was then dried and the solvent removed by evaporation. The product, recrystallized from isopropyl ether/petroleum ether, melted at 120° C. (yield 40 g). The results of analysis are as follows:
IR (KBr) 3400 cm⁻¹, NH indole; 3340 cm⁻¹, NH amide; 2860 cm⁻¹, CN; 1660 cm⁻¹

Calculated for C₁₈H₂₂N₃ClO: C=65.0%; H=6.64%; N=12.65% Found: C=64.03%; H=6.78%; N=12.60%.

(b) Preparation of 1-[(2'-indol-3''-yl-ethyl)-3-ethyl-3-cyano]-2-piperidone

In a 1 liter round-bottomed flask there were placed 22 g (0.0665 mole) of the product of step (a) above, 200 ml of tetrahydrofuran, and 300 ml of t-butanol. The mixture was cooled on ice to 0° C. and there were added, in small quantities, 8.5 g (0.076 mole) of potassium tert. butoxide. After 2 hours of stirring at room temperature, the mixture was concentrated and hydrolysed. The organic phase was extracted with methylene dichloride, washed with water, dried and the solvent removed by evaporation. The desired product, recrystallized from 50:50 ethanol/ether melted at 180° C. (yield 15 g, 80%). The results of analysis are as follows:
IR 3400 cm⁻¹, NH indole; 2260 cm⁻¹, CN; 1635 cm⁻¹,

Calculated for C₁₈H₂₃N₃O: C=73.2%; H=7.1%; N=14.2% Found: C=72.46%; H=7.15%; N=14.01%.

(c) Preparation of 1-ethyl-1-cyano-5.12b-didehydro-indolo(2,3-a)quinolizidinium perchlorate In a 1 liter flask there were placed, with stirring, 50 g (0.169 mole) of the product of step (b) above and 700 ml of phosphoryl chloride. After heating under reflux for 20 hours the mixture was concentrated and extracted 2 or 3 times with 500 ml of methylene chloride which was then removed by evaporation. The product was then taken up in 300 ml of methylene chloride and cooled on ice, and 300 ml of a solution of lithium perchlorate (1 mole) was added with vigorous stirring. There was produced a yellow precipitate which, recrystallized from methanol, melted at 260° C. (yield 44 g, 70%). The results of analysis are as follows:
IR 3400 cm⁻¹, NH indole; 2260 cm⁻¹, C≡N; 1620 cm⁻¹, C=N⊕.

(d) Preparation of 1-ethyl-1-cyano-indolo(2,3-a)quinolizidine (12b-H; 1-C₂H₅ trans-isomer)

In a 1-liter round-bottomed flask there were placed 200 ml methanol, 100 ml methylene chloride and 13.5 g (0.036 mole) of the perchlorate of step (c) above. The flask was cooled to about 5° C. and 5 g of sodium borohydrate were added in small quantities. The solution was then stirred for 2 hours at room temperature, concentrated, washed with water and extracted with methylene chloride. After drying and removing the solvent, there were obtained 8 g of yellow crystals, recrystallized from isopropyl ether, melted at 160° C. (yield 80%). The results of analysis are as follows:

| IR | 3420 cm$^{-1}$ | |
|---|---|---|
| | 3440 cm$^{-1}$ | |
| | 2760 cm$^{-1}$ | NH and Bohlmann bands |
| | 2800 cm$^{-1}$ | |
| | 2250 cm$^{-1}$ | CN |

NMR (dimethylsulphoxide d$_6$, 80 MHz), 0.86δ, 3H (t) (C$\underline{H}_3$), 3.77δ, 1H (s) ($\underline{H}$ at C$_{9a}$) 9.66δ, 1H (s) (N$\underline{H}$), Calculated for C$_{18}$H$_{21}$N$_3$: C=77.7%; H=7.2%; N=15.2%   Found:   C=77.55%;   H=7.32%; N=15.10%.

(e) Preparation of 1-ethyl-1-cyano-indolo(2,3-a)quinolizidine (12b-H; 1-C$_2$H$_5$ cis-isomer)

In a 1-liter flask there was placed 19 g of the perchlorate of step (c) above, 300 cc of 95% ethanol and 40 g of zinc powder. There was added from a flask 100 ml of concentrated hydrochloric acid. Mild reflux could be observed during the addition of the acid. The mixture was allowed to stand at room temperature for 10 hours. It was then concentrated, washed with water and extracted with methylene chloride. It was made alkaline with sodium hydroxide and filtered through Celite (Trade Mark). After decanting, drying and evaporating the solvents there were obtained 6 g of a product, insoluble in ether, melting at 250° C. The results of analysis are as follows:

IR 3410 cm$^{-1}$, (NH); 2260 cm$^{-1}$ (CN); Calculated for C$_{18}$H$_{21}$N$_3$.1/4H$_2$O:   C=76.5%;   H=7.60%; N=14.85%   Found:   C=76.59%;   H=7.80%; N=14.55%.

The ether extracts were concentrated to give 4 g (total yield 71.5%) of the cis isomer of the same product as step (d) above.

NMR (dimethylsulphoxide d$_6$, 80 MHz), 1.05δ 3H (t) (C$\underline{H}_3$), 3.45δ 1H (s) ($\underline{H}$ at C$_{9a}$), 10.32δ 1H (s) (N$\underline{H}$).

(f) Preparation of 1-ethyl-1-aminoethyl-indolo(2,3-a)quinolizidine (12b-H; 1-C$_2$H$_5$ trans-isomer II)

In a 1-liter flask there were placed 4 g of lithium aluminium hydride and 400 ml of dry ether. The flask was cooled to 0°–5° C., and there were added, in small quantities, 8.9 g of the product of step (d) above. After allowing the flask to stand for 1 hour at room temperature, there were added 60 ml dry tetrahydrofuran. The mixture was heated for 2 hours under reflux. After cooling there were added, drop by drop, 40 ml water, followed by 200 ml of methylene chloride. The mixture was stirred for 15 minutes. On filtering over Celite, drying and concentrating the filtrate there was obtained 7.2 g of white crystals which, recrystallized from ether, melted at 175° C. (80% yield). The results of analysis are as follows:

IR 3280, 3190 cm$^{-1}$, NH$_2$; 3350 cm$^{-1}$, NH indole; The CN peak at about 2250 cm$^{-1}$ was absent. Calculated for C$_{18}$H$_{25}$N$_3$: C=76.4%; H=8.85%; N=14.8% Found: C=75.85%; H=8.90%; N=15.52%.

(g) Preparation of 1-ethyl-1-aminoethyl-indolo(2,3-a)quinolizidine (12b-H; 1-C$_2$H$_5$ cis-isomer I)

To a 500 ml flask there were added 3.4 g of lithium aluminium hydride, 200 ml of ether and 100 ml of tetrahydrofuran. While cooling on ice there were added, in small quantities, 6.9 g of the cis-isomer of step (e) above. After allowing the mixture to stand for 15 hours at room temperature, the product was isolated as in step (f) above. On recrystallization from 50:50 ethyl ether/petroleum ether there was obtained 5 g of a product melting at 125° F. (yield 71%).

Calculated for C$_{18}$H$_{25}$N$_3$: C=76.4%; H=8.85%; N=14.8%   Found:   C=76.25%;   H=8.61%; N=14.43%.

EXAMPLE 3

Preparation of 1-ethoxycarbonylaminoethyl-1-ethyl-indolo(2,3-a)quinolizidine (12b-H; 1-C$_2$H$_5$ trans-isomer II) hydrochloride

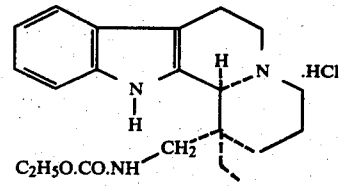

To a solution of 2 g (0.00705 mol) of the trans product II of Example 2(f) in 20 ml in dimethoxyethane, cooled to 0° C., there were alternately added, so as to maintain an alkaline pH, portions of:

800 mg of ethyl chloroformate dissolved in 5 ml of dimethoxyethane; and 750 mg of sodium carbonate dissolved in 5 ml of water.

After allowing the reaction mixture to stand for 3 hours at at room temperature, the product was extracted with dichloromethane, the dichloromethane extract was washed with water, dried and evaporated to dryness. The product was recrystallized from ethanol.

Weight: 2 g Yield: 80%. M.P.: 140° C.

IR 3210 cm$^{-1}$, amide NH; 3400 cm$^{-1}$, indole NH; 2760 and 2800 cm$^{-1}$, Bohlmann bands; 1690 cm$^{-1}$ carbamate C=O. The results of microanalysis are as follows:   Calculated   for   C$_{21}$H$_{29}$N$_3$O$_2$:   C=71.0%; H=8.17%; N=11.8% Found: C=70.94%; H=8.16%; N=11.54%.

The hydrochloride salt was formed from 2 g of the above product by adding 4 N HCl in 20 ml of ethanol.

Weight: 2 g Yield: 90% M.P.: 260° C.

removed by evaporation. The residue was taken up in dichloromethane and washed with 10% aqueous sodium hydroxide and then with water. After drying over sodium sulphate it was concentrated to give a yellowish crystalline product. The product was twice taken up in ethyl ether and centrifuged. The first stage yielded 4.6 g of crystalline product melting at 202° C., and the second stage yielded 0.8 g of crystalline product melting at 198° C. The combined products were then recrystallized from benzene to give 4.65 g of the final product.

M.P.: 204° C. Yield: 45% based on the amine (II).

TLC: 90/10; 5/10

Determination of the base with HClO₄: 100% (2 functions).

IR: 3360 cm$^{-1}$, NH; 3250 cm$^{-1}$ NH; 1620 cm$^{-1}$ C=0 urea.

Microanalysis gave the following results: Calculated for $C_{25}H_{39}N_5O$: C=70.6%; H=9.17%; N=16.45% Found: C=70.58%; H=9.20%; N=16.67%.

EXAMPLE 7

Preparation of 1-pentanoylaminomethyl-1-ethyl-indolo(2,3-a)quinolizidine (12b-H; 1—C₂H₅ trans-isomer II)

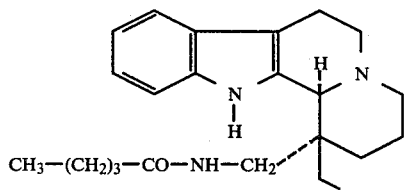

Using reaction conditions and techniques identical to those of Example 5, there were reacted a solution of 5.7 g of the trans product of Example 2(f) and 2.1 g of triethylamine in 120 ml of dichloromethane and a solution of 2.45 g pentanoyl chloride in 20 ml of dichloromethane.

There were thus obtained 7.8 g of an oil containing a little residual triethylamine.

IR: 3180–3380 cm$^{-1}$, NH; 1630–1650 cm$^{-1}$, C=0.

From the oil it was possible to obtain crystals of the product, melting at 110° C., whose analysis correspond to that of the formula.

EXAMPLE 8

Preparation of 1-pentylaminomethyl-1-ethyl-indolo(2,3-a)quinolizidine (12b-H; 1—C₂H₅ trans-isomer II)

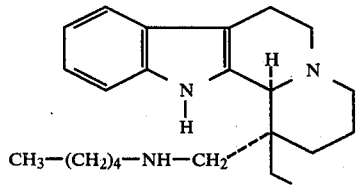

In a 500 ml three-necked flask of having a stirrer, a reflux condenser, a thermometer, and a dropping funnel there were placed 100 ml of anhydrous ethyl ether. When this had been cooled on an ice bath there were added 4 g of lithium hydride, and the contents of the flask were stirred for 15 minutes. There was then added very slowly a solution of 7.4 g of the product of Example 7 in 50 ml of anhydrous ethyl ether. The mixture was then heated under reflux for 2 hours and stirred for a further 15 hours at room temperature. It was then cooled on an ice bath and there were added dropwise 20 ml of water followed by 150 ml of dichloromethane. The mixture was then filtered over Celite, dried over sodium sulphate and concentrated by evaporation. There were obtained 7 g of an oil which could be crystallized to a product melting at 80° C.

Recrystallization from the minimum amount of isopropanol gave 4.3 g of a crystalline product melting at 97° C.

Determination of the base with HClO₄: 100% (2 functions).

Microanalysis gave the following results: Calculated for $C_{23}H_{35}N_3$: C=78.20%; H=9.92%; N=11.90% Found: C=78.18%; H=9.81%; N=12.00%.

IR basic: 3310 cm$^{-1}$, NH; 1620 cm$^{-1}$, C=0.

Dimaleate

An acid addition salt with maleic acid was prepared in solution in a mixture of isopropanol and isopropyl ether. Initially the salt formed as an oil, but could be recrystallized from ethyl acetate to give 6.7 g of the dimaleate, melting at 105° C.

Determination of the dimaleate with HClO₄: 99.6% (2 functions).

Rf: 90/10 9/10.

EXAMPLE 9

Preparation of 1-guanidinocarbonylaminomethyl-1-ethyl-indolo(2,3-a)quinolizidine (12bH; 1 C₂H₅ trans-isomer) dimaleate

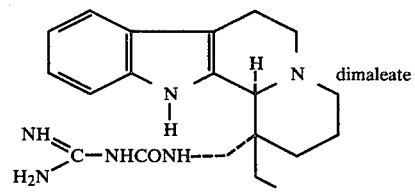

Into a 250 ml flask, 9 g of the compound prepared in Example 3, 2.2 g of guanidine base (liberated from 3 g of chlorohydrate by the ethylate-ethanol couple) are placed in 120 ml of ethanol. The mixture is refluxed for 48 hours and the solvent evaporated to dryness. The residue is taken up in a water-methylene chloride mixture, filtered on Celite and decanted, the organic phase washed first with water and then twice with a 5% acetic acid solution the acidic liquors are alkalinized with sodium bicarbonate in the presence of water; the ethereal phases are dried and evaporated.

6.4 g of a menigue-like product is obtained, which is chromatographed on silica (60 g of silica: eluant CH₂Cl₂—MeOH 80-20).

After separating 0.7 g of a first product, a second product is isolated and crystallized from ether. Yield: 3.5 g. M.P.=150° C.

IR (KBr): 3200–3400 cm$^{-1}$ wide and intense bands (νNH) 1600 cm$^{-1}$ wide band (νC=0).

The dimaleate is prepared in isopropanol.

TLC (Merck plate MP 254: eluent acetone, CHCl₃, n butanol, 25% NH₄OH 30:30:30:10

RF=0.4 1 spot

Microanalysis $C_{20}H_{28}N_6O + C_8H_8O_8$ M=600

EXAMPLE 4

Preparation of E homo azaepieburnamonine hydrochloride

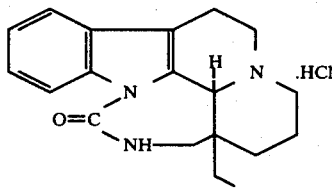

First 1-phenoxycarbonylaminomethyl-1-ethyl-indolo(2,3-a)quinolizidine (12b-H; 1-$C_2H_5$ trans-isomer) was prepared by repeating the procedure of Example 3, but replacing the ethyl chloroformate with phenyl chloroformate.

To a solution of 8 g (0.02 mol) of the product in 250 ml of tetrahydrofuran there were added 2 g of 50% sodium hydroxide. After stirring for 90 minutes, the reaction product was extracted with ethyl ether, washed with water and dried. The ethyl ether was removed by evaporation to leave 5 g of an oil, analysis of which gave the following data:

IR 3200 cm$^{-1}$, amide NH; 1670 cm$^{-1}$, amide C=O.

NMR (CCl$_4$; internal standard TMS), 0.65$\delta$ (3H,t, CH$_3$—CH$_2$), 1 to 3.2$\delta$ 15 protons solid, 3.3$\delta$ (1H, s, angular proton 12b H), 7.2$\delta$ (3H aromatic solid), 8.1$\delta$ (1H aromatic solid).

The hydrochloride was prepared by treating the above oil with hydrochloric acid in 20 ml of ethanol, followed by centrifuging. The yield was 60%, calculated on the amine (II) used as starting material. M.P.: 260° C. The product crystallized with ½ mole of water of crystallization.

The results of microanalysis are as follows:

Calculated for C$_{19}$H$_{23}$N$_3$O.HCl.0.5 H$_2$O: C=64.5%; H=7.05%; N=11.8% Found: C=64.38%; H=7.11%; N=11.62%.

EXAMPLE 5

Preparation of 1-(3',4',5'-trimethoxybenzoylaminomethyl)-1-ethyl-indolo(2,3-a)quinolizidine hydrochloride (12b-H; 1-$C_2H_5$ trans-isomer II)

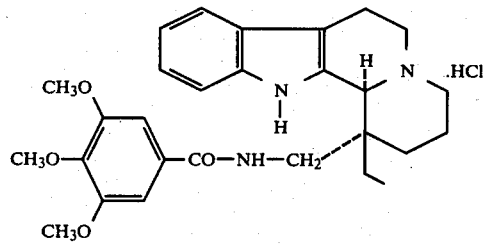

Into a 250 ml three-necked bottle of fitted with a stirrer, a CaCl$_2$ guard, a thermometer and a dropping funnel there were added 2.85 g of the trans product II of Example 2(f), 1.1 g of triethylamine and 50 ml of dichloromethane.

The mixture was stirred and cooled to 0°-2° C. At this temperature there were slowly added 2.31 g of 3,4,5-trimethoxybenzoyl chloride in 15 ml of dichloromethane. The addition took place over a period of 15 to 20 minutes, after which time the mixture was stirred for 1 hour at 0° C. then for 15 minutes at ambient temperature.

The mixture was then washed several times with water, then with 10% aqueous sodium hydroxide and then again with water. It was dried over sodium sulphate and concentrated to form a non-crystalline mass, having the texture of meringue and melting at about 100° C.

TLC: 90/10; 8/10;

IR 3230 cm$^{-1}$, NH; 3190 cm$^{-1}$, NH; 2750 and 2800 cm$^{-1}$, Bohlmann bands; 1640 cm$^{-1}$, C=O amide.

Determination of the base with HClO$_4$:97%.

To prepare the hydrochloride, the above product was dissolved in a 1:1 mixture of isopropyl ether and isopropanol, and 4 N hydrochloric acid was added. The hydrochloride precipitated while hot, and was filtered while hot and washed with ethanol to produce 4.5 g (88% yield) of the desired product.

TLC: 90/10; 8/10

M.P.: 210° C. (not in French text)

Determination of hydrochloride: 100% (1 function).

Microanalysis gave the following results:

Calculated for C$_{28}$H$_{35}$N$_3$O$_4$HCl: C=65.45%; H=7.00%; N=8.18%; Found: C=64.34%; H=7.17%; N=8.11%; C=64.15%; H=7.16%; N=7.96%.

EXAMPLE 6

Preparation of 1-(N'-[diethylaminoethyl]-N-ureidomethyl)-1-ethyl-indolo(2,3-a)quinolizidine (12b-H; 1-$C_2H_5$ trans-isomer II)

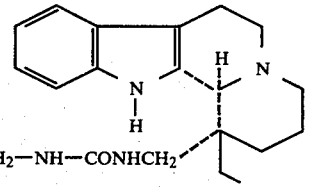

(C$_2$H$_5$)$_2$N—CH$_2$CH$_2$—NH—CONHCH$_2$

There was first prepared the corresponding 1-phenoxycarbonylaminomethyl-1-ethyl derivative: 7 g of the trans product II of Example 2(f) and 100 ml of tetrahydrofuran were placed in a 500 ml three-necked flask having a stirrer and two dropping funnels. The flask was cooled to between 0° C. and 5° C. and at this temperature, there were simultaneously added 4.25 g of phenyl chloroformate in 50 ml of tetrahydrofuran and 2.9 g of sodium bicarbonate in 50 ml of water. (The amounts added were calculated to maintain the pH at 6 to 7). The mixture was then allowed to warm to room temperature and stirring was continued for 3 hours. The product was extracted with 100 ml of dichloromethane and the extract was washed several times with water before being dried with sodium sulphate, and concentrated by evaporation. There were obtained 11 g of the product, which was an oil.

IR 3270 cm$^{-1}$, NH; 1710 cm$^{-1}$, C=O.

The 1-ureidomethyl product was prepared as follows:

Into a 500 ml flask provided with a reflux condenser, there were placed 11 g of the above oil 3.5 g of dimethylaminoethylamine and 180 ml of methanol. The amount of dimethylaminoethylamine used corresponded to a 20% excess. The mixture was heated under reflux for 2.5 hours and then the methanol was Calculated % C 56.00, H 6.00, N 14.00; Found: 56.07, 6.46, 12.59.

EXAMPLE 10

Preparation of E homo 14 azaeburnamonine (12b-H; 1—C₂H₅ cis-isomer I)

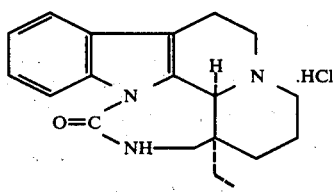

Example 4 was repeated except that the cis product (I) of Example 2(g) was used in place of the trans product (II) of Example 2(f). There was obtained 5.7 g of product (yield 69%). M.P.: 190° C.

IR: 3260 cm⁻¹, NH; 1690 cm⁻¹, C=o.

Microanalysis gave the following results: Calculated for $C_{19}H_{23}N_3O$: C=73.8%; H=7.45%; N=13.6% Found: C=73.48%; H=7.35%; N=12.99%.

The hydrochloride was obtained by adding 4 N HCl to a solution of the base in a 1:1 mixture of ethanol and ethyl ether.

EXAMPLE 11

Preparation of 1-ethoxycarbonylaminomethyl-1-ethyl-indolo(2,3-a)quinolizidine (12b-H; 1—C₂H₅ cis-isomer I) hydrochloride

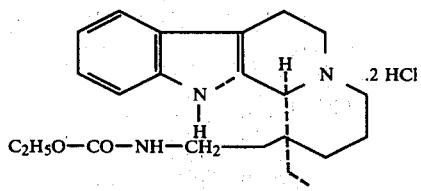

The procedure of Example 3 was repeated except that the cis product (I) of Example 2(g) was used instead of the trans product (II) of Example 2(f). There was obtained 2.1 g of the free base (84% yield). M.P.: 210° C.

IR 3400 cm⁻¹, indole NH; 3210 cm⁻¹, amide NH; 2790 and 2810 cm⁻¹, Bohlmann bands; 1690 cm⁻¹, carbamate C=0.

Microanalysis gave the following results: Calculated for $C_{21}H_{29}N_3O_2$: C=71.0%; H=8.17%; N=11.82% Found: C=70.85%; H=8.22%; N=11.94%.

NMR (CDCl₃; internal standard TMS), 1.1δ (6 H, t, CH₃ ethyl and ethyl esterS), 1.5 to 3.5δ (15H, solid), 3.9δ (2H, q, CH₂O), 5.65δ (1H, m, NH-amide), 7.25δ (4H, solid, aromatic), 7.9δ (1H, s, NH-indole).

The hydrochloride was prepared by means of 4 N hydrochloric acid in acetone.

Yield: 90%. M.P.: 250° C.

EXAMPLE 12

Preparation of 1-(N'-[diethylaminoethyl]-N-ureidomethyl)-1-ethyl-indolo(2,3-a)quinolizidine (12b-H; 1—C₂H₅ cis-isomer I)

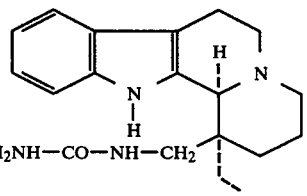

The first part of Example 6 was repeated using the cis product I of Example 2(g) instead of the trans product II of Example 2(f). The second part of Example 6 was then repeated on a smaller scale, using 3 g of the 1-phenoxycarbonylaminomethyl derivative, 1.2 g of diethylaminoethylamine and 50 ml of methanol. There was thus produced 2.8 g of the desired product which was an oil.

The hydrochloride was obtained by treatment with 4 N hydrochloric acid in acetone. The salt was isolated by concentrating the acetone solution and recrystallizing from a 1:1 mixture of ethyl acetate and ethanol.

There were obtained 1.8 g of product, melting at 250° C. Yield: 48.5% based on the weight of the amine starting material.

IR 3300 cm⁻¹; 1640 cm⁻¹.

Microanalysis gave the following results with 1 mole of water of crystallization): Calculated for $C_{25.5}H_{39}N_5O$. 2HCl. H₂O: C=58.30%; H=8.35%; N=13.74%; Found: C=58.56%; H=8.25%; N=13.60%.

Toxicity

LD 50 has been determined per os on mice. The compounds of the invention have a toxicity comparable to or less than that of vincamine. The more toxic products (LD 50: 400 mg/kg; vincamine 450 mg/kg) are those of exampls 2(f), 3 and 4; the less toxic products are those of examples 5, 10 and 12, while the remaining compounds have an intermediate toxicity.

Pharmacology

The activity of the compounds of the invention has been studied in regard to their action one femoral and vertebral blood flows, arterial pressure and cardiac rhythm. Comparison was made with vincamine and with compounds described in French patent publications 2,285,877 and 2,292,475. The tests, conducted in the same manner as used for vincamine, have shown that the compounds of the invention, and more particulrly those of examples 3 and 5

(a) induce a strong increase in femoral blood flow; the compounds described in the French patent publications have a similar action but vincamine reduces this blood flow;

(b) induce a strong increase in vertebral blood flow; the compounds described in the French patent publications do not act at all or induce a moderate increase, whereas vincamine reduces this flow;

(c) do not significantly affect the arterial blood pressure, whereas the comparison compounds lower it;

(d) induce a slight increase in cardiac rhythm whereas the compounds described in the French patent publications generally induce a greater increase and vincamine lowers this parameter.

On the basis of these results the compounds of the invention appear to have a very favourable action in the field of cerebral irrigation, which was confirmed clinically.

Dosage

The compounds of the invention may be administered i.v. or per os, at doses comparable to those used for vincamine, (dosage units of 5 to 40 mg).

I claim:

1. A method of increasing femoral blood flow and vertebral blood flow without significantly affecting arterial blood pressure and inducing only a slight increase in cardiac rhythm comprising the administration of 5 mg to 40 mgs of a compound according to the formulae (I) and (II)

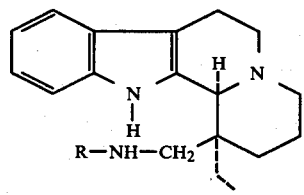
(I)

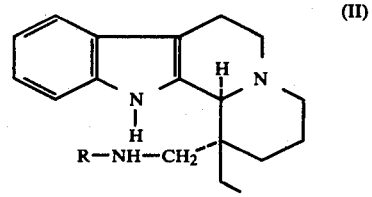
(II)

wherein R is alkoxy carbonyl, the alkoxy having up to 5 carbon atoms, trimethoxy substituted phenyl carbonyl or a therapeutically acceptable acid addition salt of one of the foregoing.

2. A therapeutic composition comprising in a therapeutically acceptable carrier, a therapeutically effective amount for increasing femoral blood flow and vertebral blood flow without significantly affecting arterial blood pressure and inducing only a slight increase in cardiac rhythm of a compound of the formulae (I) and (II)

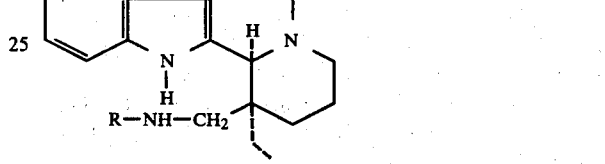
(I)

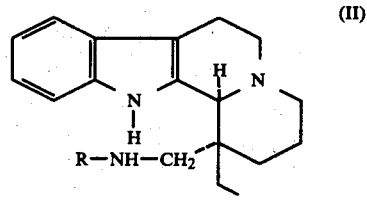
(II)

wherein R is an alkoxy carbonyl, the alkoxy having up to 5 carbon atoms, trimethoxy substituted phenyl carbonyl or a therapeutically acceptable acid addition salt of one of the foregoing.

* * * * *

UNITED STATES PATENT AND TRADEMARK OFFICE
CERTIFICATE OF CORRECTION

PATENT NO. : 4,353,911
DATED : October 12, 1982
INVENTOR(S) : Andre Buzas

It is certified that error appears in the above-identified patent and that said Letters Patent are hereby corrected as shown below:

Column 5, insert --EXAMPLE 1-- before the first line "(a) Preparation of".

Column 7, line 54: Delete "(2H) O-$\underline{CH_2}$-O" and substitute therefor --(2H) O-$\underline{CH_2}$-O--.

Column 11, line 17: Delete ($\underline{H}$ at $C_{9\underline{a}}$)" and substitute therefor: --($\underline{H}$ at $C_{9\underline{a}}$)--.

Column 11, line 46: Delete ($\underline{H}$ at $C_{9\underline{a}}$)" and substitute therefor --($\underline{H}$ at $C_{9\underline{a}}$)--.

Column 12, Example 3: Delete the formula therein and substitute the following:

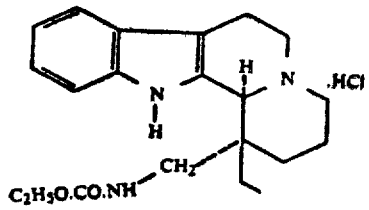

Column 13, line 30: Delete "angular proton 12b H)" and substitute therefor --angular proton 12$\underline{b}$H)--.

Column 14, line 21: Delete "(not in French text)".

UNITED STATES PATENT AND TRADEMARK OFFICE
CERTIFICATE OF CORRECTION

PATENT NO. : 4,353,911
DATED : October 12, 1982
INVENTOR(S) : Andre Buzas

It is certified that error appears in the above-identified patent and that said Letters Patent are hereby corrected as shown below:

Column 14, Example 6: Delete the formula therein and substitute the following:

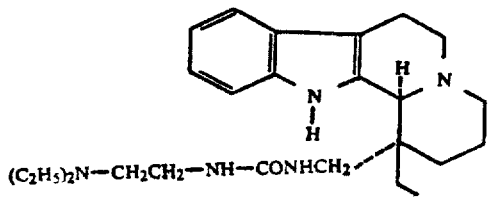

Column 16, line 53: Delete "acid solution the" and substitute therefor --acid solution. The--.

Column 16, line 54: Delete "water" and substitute therefor --ether--.

Column 16, line 56: Delete "menigue-like" and substitute therefor --merigue-like--.

Column 17, line 23: Delete "C=o" and substitute therefor --C=O--.

UNITED STATES PATENT AND TRADEMARK OFFICE
CERTIFICATE OF CORRECTION

PATENT NO. : 4,353,911

DATED : October 12, 1982

INVENTOR(S) : Andre Buzas

It is certified that error appears in the above-identified patent and that said Letters Patent are hereby corrected as shown below:

Column 17, Example 11: Delete the formula therein and substitute the following:

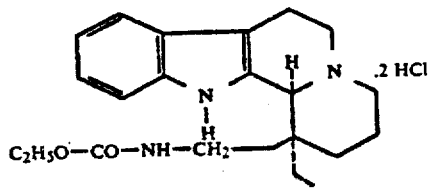

Column 18, line 33: Insert "(" before --with 1 mole of--.

Column 18, line 34: Delete "$C_{25s}H_{39}N_5O$" and substitute therefor --$C_{25}H_{39}N_5O$--.

Column 18, line 43: Delete "exampls" and substitute therefor --examples--.

Column 18, line 49: Delete "one" and substitute therefor --on--.

Signed and Sealed this

Third Day of May 1983

[SEAL]

Attest:

GERALD J. MOSSINGHOFF

Attesting Officer    Commissioner of Patents and Trademarks